United States Patent

Riva et al.

[11] 4,013,679
[45] Mar. 22, 1977

[54] SUBSTITUTED 6,7-DIHYDRO [1,7-ab](1) BENZAZEPINE COMPOUNDS

[75] Inventors: Mario Riva, Monza (Milan); Luciano Toscano, Milan; Giampiero Grisanti, Milan; Alberto Bianchetti, Milan, all of Italy

[73] Assignee: Pierrel S.p.A., Milan, Italy

[22] Filed: June 30, 1975

[21] Appl. No.: 591,763

[30] Foreign Application Priority Data

July 3, 1974 United Kingdom ............ 29419/74

[52] U.S. Cl. .................... 260/326.9; 204/158 R; 260/326.31; 260/326.5 B; 424/274
[51] Int. Cl.² ................................. C07D 487/06
[58] Field of Search ............... 260/326.85, 326.9; 424/274; 204/158 R, 165, 177

*Primary Examiner*—Donald G. Daus
*Assistant Examiner*—Mary C. Vaughn
*Attorney, Agent, or Firm*—Bacon & Thomas

[57] ABSTRACT

This invention relates to compounds of the formula:

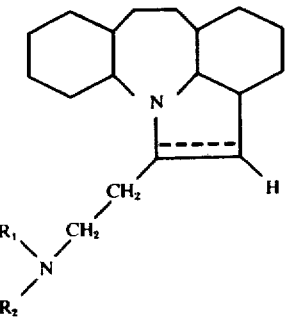

wherein $R_1$ and $R_2$ may be the same or different and include hydrogen, methyl, and benzyl, their method of preparation, and pharmaceutical compositions containing these compounds.

9 Claims, No Drawings

SUBSTITUTED 6,7-DIHYDRO [1,7-ab](1) BENZAZEPINE COMPOUNDS

This invention relates to chemical compounds which possess valuable therapeutic utility as antidepressant agents.

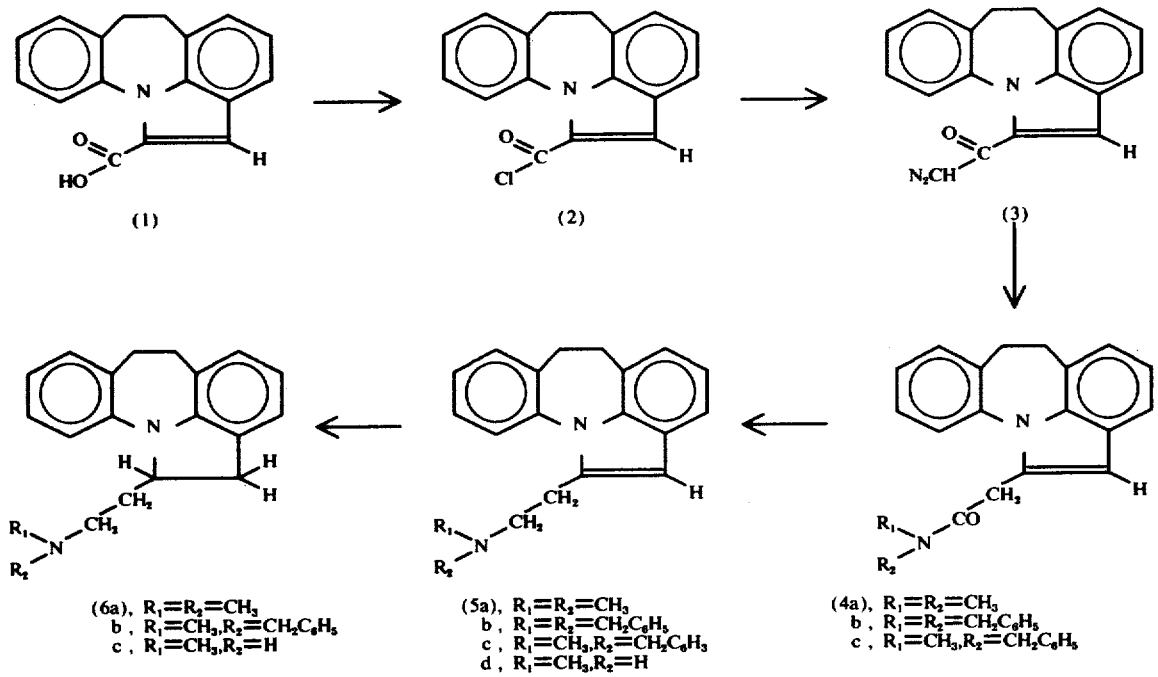

SCHEME I (6a), $R_1=R_2=CH_3$
 b , $R_1=CH_3, R_2=CH_2C_6H_5$
 c , $R_1=CH_3, R_2=H$ (5a), $R_1=R_2=CH_3$
 b , $R_1=R_2=CH_2C_6H_5$
 c , $R_1=CH_3, R_2=CH_2C_6H_5$
 d , $R_1=CH_3, R_2=H$ (4a), $R_1=R_2=CH_3$
 b , $R_1=R_2=CH_2C_6H_5$
 c , $R_1=CH_3, R_2=CH_2C_6H_5$

In another aspect, this invention relates to a method of preparing the compounds which combine the features of an indole or an indoline with those of the dihydrodibenz [b,f] azepine system found in the clinically useful antidepressant imipramine, 5-(3-dimethylaminopropyl)-10,11-dihydro-5H-dibenz[b,f]azepine.

The structure I indicates the manner in which the basic sidechain of imipramine is bound to the polycyclic system containing the indole ring or the indoline ring of this invention;

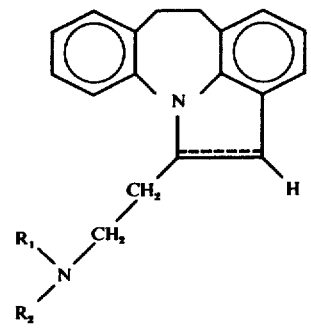

wherein
$R_1$ is hydrogen, methyl, benzyl groups
$R_2$ is hydrogen, methyl, benzyl groups
These compounds show a remarkable imipramine-like activity with a low toxicity.

The compounds of the present invention also are devoid of anticholinergic activity typical of imipramine which is generally accepted to be an undesirable side effect in clinical use. These features make the present compounds particularly interesting and potentially useful in the treatment of depressive syndromes. The polycyclic indole and indoline compounds (I) of this invention may be synthesized as illustrated in the following reaction Scheme I:

Referring to the reaction scheme, the known starting material 6,7-dihydroindolo [1,7-ab] [1] benzazepine-1-carboxylic acid (1) was transformed into the acid chloride (2) by treatment with an acyl halide followed by treatment with diazomethane to give the diazoketone (3).

The amides (4a), (4b) and (4c) were obtained in good yields by a photo-chemical Wolff rearrangement of compound (3) in a suitable solvent such as an alcohol and in the presence of a lower alkyl or aralkyl amine such as dimethylamine, N-dibenzylamine or N-benzylmethylamine. These amides were reduced with a reducing agent such as $AlLiH_4$, into compounds (5a), (5b) and (5c). Catalytic debenzylation of the benzylic derivative (5c) using as a catalyst palladium-charcoal gave the compound (5d).

The indole compounds (5a), (5c) and (5d) were reduced by a sodium-ammonia reduction to yield the desired polycyclic indolines (6a), (6b) and (6c). Moreover, the compound (6c) can be obtained also by the above catalytic debenzylation of the benzylic derivative (6b).

The pharmaceutically acceptable acid addition salts of the compounds may be conveniently formed by conventional techniques. Such acid addition salts may be formed from such acids as hydrochloric acid, phosphoric acid, hydrobromic acid, nitric acid, sulfamic acid, formic acid, citric acid, lactic acid, malic acid, maleic acid, succinic acid, tartaric acid, acetic acid, trifluoroacetic acid, benzoic acid, gluconic acid, ascorbic acid, sulfonic acid, para-toluenesulfonic acid, fumaric acid, meconic acid, methanesulfonic acid, and the like.

The antidepressant action of the compounds was evaluated by measuring the antagonism to Reserpine induced hypothermia and ptosis in mice. These pharmaceutical tests are in fact considered to be predictive of antidepressant activity in man.

In the hypothermia test Reserpine was administered at the dose of 5 mg/kg i.p. 18 hours before the oral administration of the compounds according to Askew B.M. (Life Sci., 10, 725, 1963). In the ptosis test Reserpine was given intravenously at the dose of 1.5 mg/kg one hour after the oral administration of the compounds. (Rubin B. et alt. — J. Pharmacol Exp. Ther., 120, 125, 1957). All drugs displayed activity at a dose level ranging from 1.25 to 10 mg/kg p.o. Imipramine, used as reference compound, exhibits activity at about the same dose range.

The acute toxicity of the compounds of the present invention was determined in mice by oral administration. The obtained $LD_{50}s$ (Litchfield Y. T. and Wilcoxon F. — J. Pharmacol. Exp. Ther., 96, 99, 1949) vary from 200 mg/kg to values higher than 4000 mg/kg. More particularly the compounds (5$b$), (5$c$) and (6$b$) in the form of their acid addition salts, the hydrochloride, have a very low toxicity ($LD_{50} \geq 1000$ mg/kg) in comparision with that of Imipramine ($LD_{50} = 400$ mg/kg). Therefore these compounds show a more favorable therapeutic index $$\frac{LD_{50}}{ED_{50}}$$

than that of Imipramine itself.

Moreover, the compounds tried on other conventional tests, proved to be inactive in antagonising the convulsions evoked by Cardiazol and Strichnine in mice according to Everett G. M. and Richards R. K. (J. Pharmacol Exp. Ther., 81, 402, 1944) and Kerley T. L., et al. (J. Pharmacol. Exp. Ther., 132, 360, 1961), respectively.

In the "in vitro tests" for spasmolytic activity the compounds were inactive against Acetylcholine and Histamine induced contractions on guinea-pig ileum, up to doses 500–1000 times higher than those of the specific antagonists (Atropine and Diphenylhydramine respectively). On the contrary, Imipramine exhibits a remarkable antihistaminic as well as a weak anticholinergic action.

With regard to the antiserotonine activity, the compounds of the present invention are active at about the same concentrations range as Impramine (2–10 γ/ml). The substances of the present invention can be administered as such or conveniently mixed with known inert vehicles (pharmaceutically acceptable carrier) for the preparation of usual pharmaceutical forms, such as: tablets, coated tablets, pills, capsules, timed-release pellets and the like. Aqueous solutions or suspensions thereof can be administered both orally and parenterally.

The following examples serve to illustrate the invention without limitation thereon.

EXAMPLE 1

7.9 g. (0.030 moles) of 6,7-dihydroindolo [1,7-ab] [1] benzazepine-1-carboxylic acid (1) was refluxed in 60 ml. of dry benzene and 11.9 g. (0.100 moles) of thionyl chloride for 3 hours.

The solution was then evaporated and 8.7 grams of 6,7-dihydroindolo [1,7-ab] [1] benzazepine-1-carbonyl chloride (2) was obtained and characterized by: IR (liquid film) 1760 (broad), 1600, 1590, 1580, 805, 760, 740, 720, 685, 660 cm$^{-1}$. This product was used as such for the preparation of compound 3.

EXAMPLE 2

9 g. (0.030 moles) of 6,7-dihydroindolo [1,7-ab] [1] benzazepine-1-carbonyl chloride (2) were added at 0°–5° C to a solution of 5.9 g. (0.140 moles) of diazomethane in 270 ml. of ethylether. After several hours at 20°–25° C the ether was evaporated under reduced pressure and the crude product was purified by column chromatography on FLORISIL (Registered Trademark) (ratio 1:30) with benzene as eluant.

The collected fractions give 7.6 g. of 2-diazo-1-(6,7-dihydroindolo [1,7-ab] [1] benzazepine-1-yl)-ethanone (3) characterized by IR(KBr) 2100, 1600, 1540, 830, 770, 750, 730, 710, 640 cm$^{-1}$. Analysis: Calcd. for $C_{18}H_{13}N_3O$ (percent) C 75.24; H 4.56; N 14.63; Found (percent) C 75.32; H 4.50; N 14.73.

EXAMPLE 3

4.5 g. (0.015 moles) of 2-diazo-1-(6,7-dihydroindolo [1,7-ab] [1] benzazepine-1-yl)-ethanone (3) were dissolved in 1600 ml. of ethanol and 135 g. (3 moles) of dimethylamine.

The mixture was photolized with actinic radiation (lamp 3500 A°) at 10°–20° C for 2–3 hours and the compound (4$a$) was isolated by evaporation to dryness of the mixture followed by purification by column chromatography on alumina B. III (ratio 1:30) benzene as eluant.

Evaporation of the first eluates yielded 2 g. of 6,7-dihydroindolo-[1,7-ab] [1] benzazepine-1-dimethylacetamide (4$a$) characterized by:

IR (liquid film) 1650 (broad), 1610, 1580, 1560, 800, 770, 755, 740, 860 cm$^{-1}$. MMR (CDCL$_3$) Hz at 60 mHz 450–410 (m, 7, ArH) 400, 399, 398 (triplet, 1, H at position 2(236 (S, broad, 2, >NCOCH$_2$) 190 (S, 4, ArCH$_2$ CH$_2$Ar) 174 (S, 3, >NCH$_3$) 165 (S, 3, >NCH$_3$). Analysis: Calcd. for $C_{20}H_{20}N_2O$ (percent) C 78.92; H 6.62; N 9.20; Found (percent) C 79.07; H 6.71; N 9.08.

EXAMPLE 4

3 g. (0.010 moles) of 2-diazo-1-(6,7-dihydroindolo[1,7-ab] [1] benzazepin-1-yl)-ethanone (3) were dissolved in 650 ml. of ethanol and 84 g. (0.4 moles) of N-dibenzylamine. The mixture was photolized (lamp 3500 A°) at 10°–20° C for 4 hours and the compound (4$b$) was isolated by evaporation to dryness and purified by column chromatography on alumina B. III (ratio 1:100) with benzene as eluant.

Evaporation of the first eluates yielded 1.8 g. 6,7-dihydroindolo [1,7-ab] [1] benzazepine-1-dibenzylacetamide (4$b$) characterized by:

IR (liquid film) 1650 (broad), 1605, 1580, 800, 750, 700, 670cm$^{-1}$. Analysis: Calcd. for $C_{32}H_{28}N_2O$ (percent) C 84.18; H 6.18; N 6.14; Found (percent) C 83.99; H 6.08; N 6.23.

EXAMPLE 5

9 g. (0.03 moles) of 2-diazo-1-(6,7-dihydroindolo [1,7-ab] [1] benzazepin-1-yl)-ethanone (3) were dissolved in 1100 ml. of ethanol and 145 g. (1.2 moles) of N-benzylmethylamine. The mixture was photolized (lamp 3500 A°) at 10°–20° C for 4 hours and the compound (4c) was isolated by evaporation to dryness and purified by column chromatography on alumina B. III (ratio 1:50) with benzene as eluant.

Evaporation of the first eluated yielded 4.5 g. of 6,7-dihydroindolo [1,7-ab] [1] benzazepine-1-(N-benzyl-N-methyl acetamide) (4c) characterized by:

IR (liquid film) 2860, 1650, 1605, 1580, 800, 775 (broad) 700, 670 cm$^{-1}$. NMR (CDCl$_3$) Hz at 60 mHz 450–400 (m, 13, H at position 2 and ArH) 272, 256 (d, 2, >NCH$_2$Ar) 240–237(m, 2, >NCOCH$_2$) 188, 183 (d, 4, ArCH$_2$CH$_2$Ar) 174, 160 (d, 3, >NCH$_3$). Analysis: Calcd. for C$_{26}$H$_{24}$N$_2$O (percent) C 82.07; H 6.36; N 7.36. Found (percent) C 82.21; H 6.43; N 7.40.

EXAMPLE 6

A solution of 2.13 g. (0.007 moles) of 6,7-dihydroindolo [1,7-ab] [1] benzazepine-1-dimethylacetamide (4a) in 60 ml. of dry ethylether was added dropwise to a suspension of 1.07 g. (0.028 moles) of AlLiH$_4$ in 60 ml. of dry ethylether. After refluxing under stirring for 2 hours the mixture was cooled and decomposed with water added at a rate so as to just maintain a gentle reflux of ethylether. When all hydrogen has been evolved, a slight excess of water was added and the mixture was stirred for 30 minutes at room temperature. The inorganic material was removed by filtration and washed with ethylether.

The ether solution was dried and then evaporated. The oily residue (1.9 g.) was purified by column chromatography on alumina B. III. (ratio 1:50) with cyclohexane-chloroform (1:1) as eluant. Evaporation of the first eluates yielded 2 g. of 1-[2-(dimethylamino)ethyl]-6,7-dihydro-indolo [1,7-ab] [1] benzazepine (5a) characterized by:

IR (liquid film) 2820, 2700, 1585, 1560, 810, 750 (broad) 670 cm$^{-1}$. NMR (CDCl$_3$) Hz at 60 mHz 450–410 (m, 7H, ArH) 393 (S broad, 1, H at position 2) 200–150 (m, 4, >NCH$_2$CH$_2$) 190 (S, 4, ArCH$_2$CH$_2$Ar) 133 (S, 6, CH$_3$NCH$_3$). The oily product was converted into the hydrochloride. Analysis: Calcd. for C$_{20}$H$_{22}$N$_2$·HCl (percent) C 73.50; H 7.09; N 8.57. Found (percent) C 73.59; H 7.05; N 8.50.

EXAMPLE 7

A solution of 1.83 g. (0.004 moles) of 6,7-dihydroindolo [1,7-ab] [1] benzazepine-1-dibenzylacetamide (4b) in 15 ml. of dry ethylether was added dropwise to a suspension of 0.61 g. (0.016 moles) of AlLiH$_4$ in 10 ml. of dry ethylether. It was refluxed under stirring for 3 hours and the mixture, after cooling, was employed according to the general procedure of Example 6. The compound 1-[2-(dibenzylamino)ethyl]-6,7-dihydroindolo [1,7-ab] [1] benzazepine (5b) thus obtained was converted into the hydrochloride which is characterized as follows:

M.P. 188°–90° C (decomposition) IR (KBr) 250 (broad), 1605, 1580, 1560, 750, 700 cm$^{-1}$. Analysis: Calcd. for C$_{32}$H$_{30}$N$_2$·HCl (percent) C 80.23; H 6.52; N 5.85; Found (percent) C 80.32; H 6.40; N 5.63.

EXAMPLE 8

A solution of 3.42 g. (0.009 moles) of 6,7-dihydroindolo [1,7-ab] [1] benzazepine-1-(N-benzyl-N-methylacetamide) (4c) in 25 ml. of dry ethylether was added dropwise to a suspension of 1.37 g. of AlLiH$_4$ (0.036 moles) in 15 ml. of dry ethylether. It was refluxed under stirring for one hour and the mixture, after cooling, was converted using the general procedure of Example 6 into the compound 1-[2-(N-benzyl-N-methylamino)ethyl]-6,7-dihydroindolo[1,7-ab] [1] benzazepine (5c), which in turn was converted into the hydrochloride which is characterized as follows:

M.P. 185°–7° C (2.9 g.), raised by crystallization from methanol-ethylether to 199°–201° C.

IR (KBr) 2400 (broad), 1600, 1580, 1560, 770, 760, 750, 745, 740, 700 cm$^{-1}$. Analysis: Calcd. for C$_{26}$H$_{26}$N$_2$·HCl (percent) C 77.50; H 6.75; N 6.95; Found (percent) C 77.59; H 6.83; N 6.92.

EXAMPLE 9

2.02 g. (0.005 moles) of 1-[2-(N-benzyl-N-methylamino)ethyl]-6,7-dihydroindolo [1,7-ab] [1] benzazepine (5c) hydrochloride in 200 ml. of methanol was hydrogenated for 23 hours over 0.700 g. of 5% Palladium-charcoal at 20° C and 1 Atm. Filtration and evaporation gave a crude product (1.8 g.) which by crystallization from methanol-ethylether gave 1.2 g. of 1-[2-(methylamino)ethyl]-6,7-dihydroindolo [1,7-ab] [1] benzazepine (5d) hydrochloride, characterized by:

M.P. 185°–7° C. IR(KBr) 2750 (broad), 2430, 1605, 1595, 1585, 1555, 830, 760, 745, 740, 720, 660 cm$^{-1}$. Analysis: Calcd. for C$_{19}$H$_{20}$N·HCl (percent) C 72.95; H 6.77; N 8.95; Found (percent) C 72.83; H 6.71; N 8.90.

EXAMPLE 10

1.16 g. (0.004 moles) of 1-[2-(dimethylamino)ethyl]-6,7-dihydroindolo [1,7-ab] [1] benzazepine (5a) was dissolved in a mixture of 10 ml. of dry tetrahydrofuran and 20 ml. of liquid ammonia at −40° C. The solution was treated with 0.414 g. (0.018 moles) of sodium, added in small pieces during 30 minutes (blue colour). After another 15 minutes the mixture was treated with an excess of ammonium chloride and evaporated. The residue was treated with water and chloroform.

The chloroform solution was washed successively with water, dried and evaporated to dryness under vacuum at 60° C. The yellow oily residue was purified by column chromatography on alumina B.II (ratio 1:50) with cyclohexane-chloroform (8:2) as eluant.

Evaporation of the first eluates yielded 0.7 g. of 1-[2-(dimethylamino)ethyl]-1,2,6,7-tetrahydro-indolo[1,7-ab] [1] benzazepine (6a); characterized by:

IR (liquid film) 2820, 2760, 1600, 1575, 760, 730 cm$^{-1}$. NMR (CDCl$_3$) Hz at 60 mHz 440–380 (m, 7, ArH) 300–275 (m, 1, H at position 1) 220–90 (m, 6, NCH$_2$CH$_2$ and 2H at position 2) 180 (S, 4, ArCH$_2$CH$_2$Ar) 130 (S, 6, CH$_3$NCH$_3$). The oily product was converted into the hydrochloride. Analysis: Calcd. for C$_{20}$H$_{24}$N$_2$·HCl (percent) C 73.04; H 7.66; N 8.52; Found (percent) C 72.89; H 7.78; N 8.37.

EXAMPLE 11

0.805 g. (0.002 moles) of 1-[2-(N-benzyl-methylamino) ethyl]-6,7-dihydroindolo [1,7-ab] [1] benzazepine (5c) hydrochloride was dissolved in a mixture of 6 ml. of dry tetrahydrofuran and 15 ml. of liquid ammonia at −40° C.

The solution was treated with 0.100 g. (0.0044 moles) of sodium, added in small pieces during 30 minutes (blue colour). After another 30 minutes the mixture was treated using the general procedure of Example 10. The yellow oily residue of 1-[2-(N-benzyl-N-methylamino)ethyl]-1,2,6,7-tetrahydroindolo [1,7-ab] [1] benzazepine (6b) was converted into the hydrochloride (0.850 g.); characterized by:

IR (liquid film) 2700, 1595, 1580, 750 (broad) 720, 700 cm$^{-1}$. Analysis: Calcd. for $C_{26}H_{28}N_2 \cdot HCl$ (percent) C 77.11; H 7.22, N 6.92; Found (percent) C 76.98; H 7.31; N 7.02.

EXAMPLE 12

1.56 g. (0.005 moles) of 1-[2-(methylamino)ethyl]-6,7-dihydroindolo [1,7-ab] [1] benzazepine (5d) hydrochloride was dissolved in a mixture of 70 ml. of dry tetrahydrofuran and 30 ml. of liquid ammonia at $-40°$ C. The solution was treated with 0.255 g. (0.011 moles) of sodium, added in small pieces during 30 minutes (blue colour). After another 30 minutes the mixture was treated using the general procedure of Example 10.

The yellow oily residue (1 g.) of 1-[2-(methylamino)ethyl]-1,2,6,7-tetrahydoindolo [1,7-ab] [1] benzazepine (6c) thus obtained was converted into the hydrochloride, characterized by:

M.P. 201°–2° C.

IR (KBr) 2750 (broad), 2440, 1595, 1575, 760, 750, 740, 720 cm$^{-1}$. Analysis: Calcd. for $C_{19}H_{22}N_2 \cdot HCl$ (percent) C 72.48; H 7.36; N 8.90; Found (percent) C 72.53; H 7.41; N 8.68.

EXAMPLE 13

1.62 g. (0.004 moles) of 1-[2-(N-benzyl-N-methylamino)ethyl]-1,2,6,7-tetrahydroindolo [1,7-ab] [1] benzazepine (6b) hydrochloride in 180 ml. of methanol was hydrogenated for 22 hours over 0.5 g. of 5% Palladium-charcoal at 20° C and 1 Atm. Filtration and evaporation gave 1.3 g. of 1-[2-(methylamino)ethyl]-1,2,6,7-tetrahydroindolo [1,7-ab] [1] benzazepine (6c) the hydrochloride of which resulted to be identical to that obtained according to Example 12.

Having now fully described the invention, it will be apparent to one of ordinary skill in the art that many changes and modifications can be made thereto without departing from the spirit or scope of the invention as set forth herein.

We claim:

1. An indole or indoline compound having the formula:

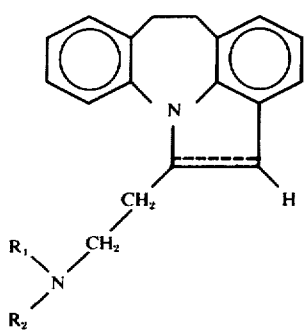

wherein $R_1$ and $R_2$ are the same or different and are hydrogen, methyl or benzyl and the pharmaceutically acceptable acid addition salts thereof.

2. A compound of claim 1, wherein $R_1$ and $R_2$ are the same and are benzyl.

3. A compound of claim 1, wherein $R_1$ is methyl and $R_2$ is benzyl.

4. The compound of claim 1, which is an indoline and wherein $R_1$ is methyl and $R_2$ is benzyl.

5. A process for the preparation of the indole compound of claim 1, which comprises the steps of exposing a compound of the formula:

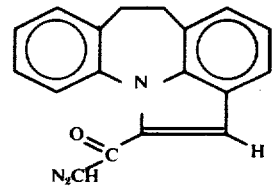

to actinic radiation in the presence of dimethylamine, N-dibenzylamine or N-benzylmethylamine to yield an amide having the formula:

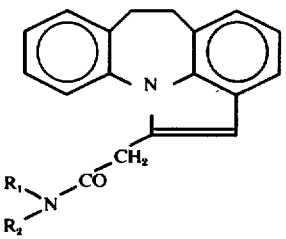

wherein $R_1$ and $R_2$ are the same or different and are hydrogen, methyl, or benzyl; reducing said amide to the indole compound of claim 1.

6. A process for the preparation of the indoline compound of claim 1, which comprises the steps of exposing a compound of the formula:

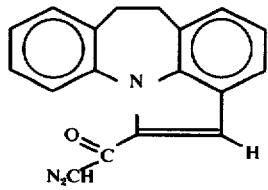

to actinic radiation in the presence of dimethylamine, N-dibenzylamine or N-benzylmethylamine to yield an amide having the formula:

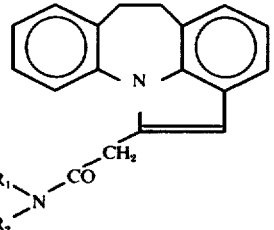

wherein $R_1$ and $R_2$ are the same or different and are hydrogen, methyl, or benzyl; reducing said amine to an indole compound having the formula

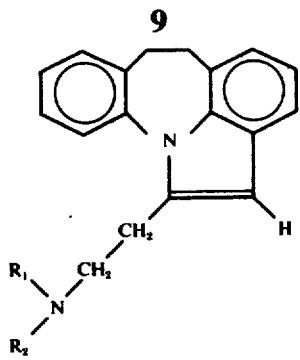

and then further reducing said indole compound to provide the polycyclic indolines of claim 1.

7. The process of claim 5, wherein the amide is reduced with AlLiH₄ to give the indole.

8. The process of claim 6, wherein the indole is reduced to the indoline using sodium-ammonia reduction.

9. Pharmaceutical compositions for relief of depressive syndromes comprising an anti-depressive amount of an active compound according to claim 1 together with a pharmaceutically acceptable carrier.

* * * * *